US005645602A

United States Patent [19]

Albrektsson et al.

[11] Patent Number: 5,645,602

[45] Date of Patent: Jul. 8, 1997

[54] KNEE JOINT PROSTHESIS

[75] Inventors: Björn Albrektsson, Onsala; Lars Valter Carlsson, Kullavik; Carl Magnus Gösta Jacobsson, Göteborg; Tord Valter Röstlund, Kullavik; Stig Gösta Wennberg, Angered, all of Sweden

[73] Assignee: Astra Aktiebolag, Sodertalje, Sweden

[21] Appl. No.: 343,423

[22] PCT Filed: May 19, 1993

[86] PCT No.: PCT/SE93/00451

§ 371 Date: Dec. 14, 1994

§ 102(e) Date: Dec. 14, 1994

[87] PCT Pub. No.: WO93/24079

PCT Pub. Date: Dec. 9, 1993

[30] Foreign Application Priority Data

May 27, 1992 [SE] Sweden .................................. 9201671

[51] Int. Cl.$^6$ ........................................ A61F 2/38

[52] U.S. Cl. ........................................ 623/20

[58] Field of Search .................................. 623/18, 19, 20, 623/21

[56] References Cited

U.S. PATENT DOCUMENTS

| | | | |
|---|---|---|---|
| 4,795,468 | 1/1989 | Hodorek et al. . | |
| 4,838,891 | 6/1989 | Branemark et al. . | |
| 4,944,757 | 7/1990 | Martinez et al. | 623/20 |
| 4,950,298 | 8/1990 | Gustilo et al. | 623/20 |
| 5,037,439 | 8/1991 | Albrektsson et al. . | |
| 5,080,674 | 1/1992 | Jacobs et al. . | |
| 5,108,442 | 4/1992 | Smith | 623/20 |
| 5,271,737 | 12/1993 | Baldwin et al. | 623/20 |

FOREIGN PATENT DOCUMENTS

| | | | |
|---|---|---|---|
| 2823406 | 11/1988 | Germany . | |
| 2223174 | 4/1990 | United Kingdom | 623/20 |

*Primary Examiner*—Michael J. Milano
*Attorney, Agent, or Firm*—White & Case

[57] ABSTRACT

The invention relates to a joint prosthesis for permanent anchorage in the bone tissue of one of the articulatory parts of a joint in a human body, in particular the femur side of a knee joint, primarily intended to be fitted in one operation only. The prosthesis comprises an attachment part (1), intended to be anchored in the human bone tissue by means of a fixture (8), and an articulation element (2) adapted to fit the attachment part (1). The articulation element is attached to the attachment part by a combination of complementary shapes (27, 28, 33, 34) and snap-action locking means (31).

5 Claims, 2 Drawing Sheets

Fig. 5
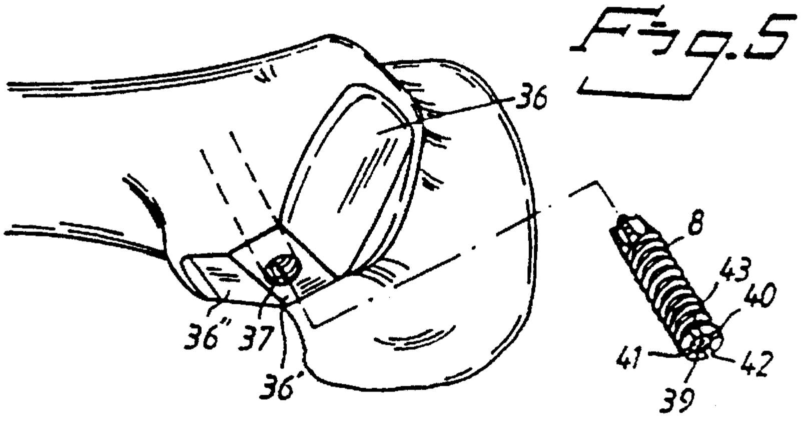
Fig. 6
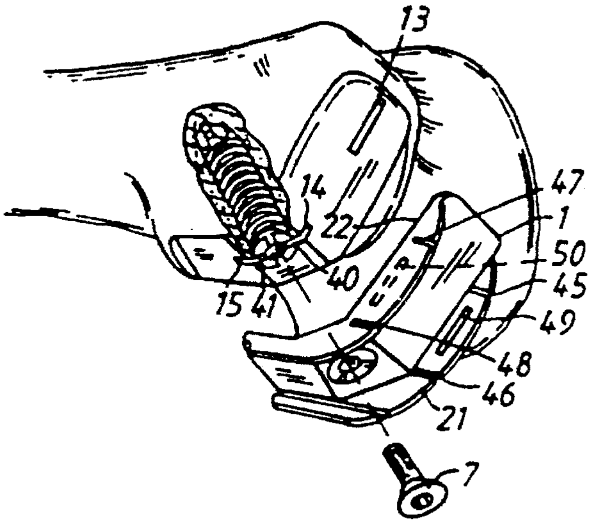
Fig. 9
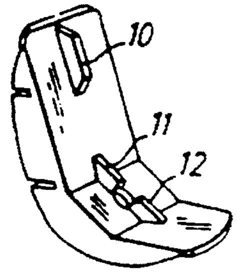
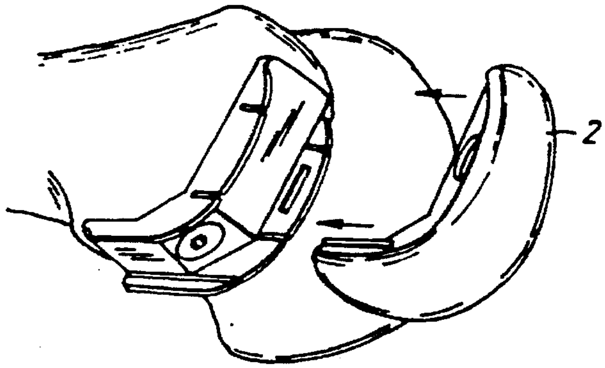
Fig. 7
Fig. 8
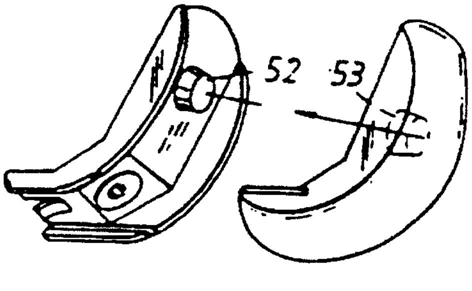

KNEE JOINT PROSTHESIS

TECHNICAL FIELD OF THE INVENTION

The invention relates to a joint prostesis for permanent anchorage in the bone tissue of one of the articulatory parts of a joint in a human body, in particular the femur side of a knee joint, primarily intended to be fitted in one operation only, wherein said prosthesis comprises an attachment part, intended to be anchored in the human bone tissue by means of a fixture, and an articulation element adapted to fit the attachment part.

BACKGROUND OF THE INVENTION

The present invention is a development of a joint prosthesis of the kind disclosed in U.S. Pat. No. 5,037,439, to Albrektsson et al. This document thus inter alia discloses a femoral part of a knee joint prosthesis comprising an articulation element having an inner surface in the shape of an L. This L-shaped articulation element comprises two essentially planar parts oriented perpendicularly to each other intended to be connected to a L-shaped recess cut in the femur bone tissue. The prosthesis also comprises an elongate intermediate element with a first side intended to bear against the vertical part of the L-shaped recess in the bone by means of at least one fixture, and a second opposite side intended to bear against one of the planar parts of the articulation element. The intermediate element is in the shape of an attachment bar having flanges provided on said second side intended as a means for holding the articulation element. The back part of the articulation element is also provided with an elongated means for attachment, having a T-shaped cross section area, intended to be inserted in said attachment bar and be locked in a predetermined position by a locking device which consists of locking lugs in the flanges of the intermediate element.

This prior art discloses a femoral part of a knee joint prosthesis which can be fitted in one operation only, which is advantageous since two operations may entail a greater risk of infection and are troublesome for the patient.

The present invention is an improvement of the prosthesis described above. Due to its shape it has a large area for osseointegration resulting in a good osseointegration in the bone tissue and thus a stable and resistant anchoring in the femur. The parts of the prosthesis all have a relatively simple construction and are easy to fit during one operation. The fitting of the articulation element to the attachment part is also simple and stable.

Other similar prior art is disclosed for instance in EP 0 183 669.

BRIEF DESCRIPTION OF THE INVENTION

The joint prosthesis of the invention is characterized in that the attachment part comprises a first and a second essentially planar parts oriented generally at an angle relative to each other and joined by means of an intermediate part, said attachment part having an inner surface intended to bear on the bone tissue, and an outer surface intended to support the articulation element, said outer surface being provided with flanges at the two sides oriented mainly in parallel with the directon of the articulational movment of the joint, said flanges are each being provided with a groove being parallel with one of said planar parts which groove is intended to guide and hold corresponding beads or flanges on said articulation element when said articulation element is slid onto said attachment part, said attachment part also being provided with a locking device for locking said articulation element when said element entirely has been slid onto said attachment part, said articulation element having a surface being shaped complementary to said outer surface of the attachment part, said beads projecting from one respective side of said articulation element and having a shape complementary to the shape of said grooves in said flanges.

The joint prosthesis according to the invention preferably is used in the human knee joint, as a femoral prosthesis, but it can also be used in other similar joints.

BRIEF DESCRIPTION OF THE APPENDED DRAWINGS

FIGS. 5–9 show the different parts of the joint in perspective views.

DETAILED DESCRIPTION OF A PREFERRED EMBODIMENT OF THE INVENTION

Figure 1:
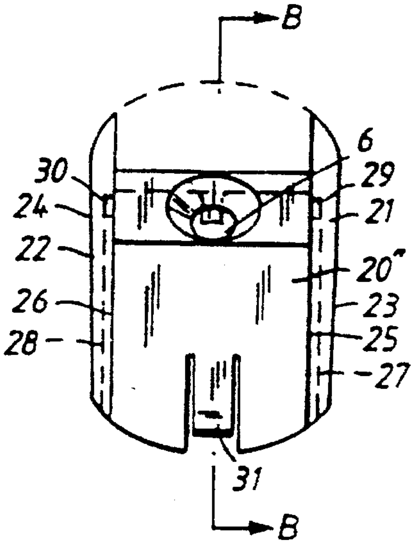
FIG. 1 show one view of an attachment part.
Figure 2:
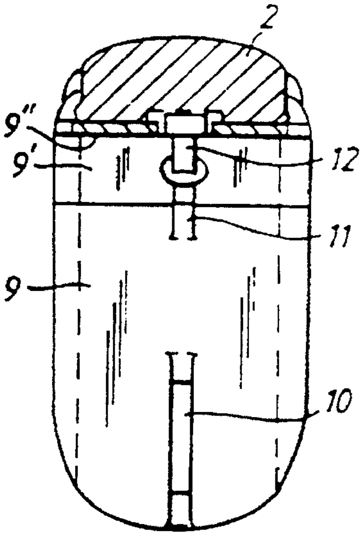
FIG. 2 shows a section along the line A—A in FIG. 3
Figure 3:
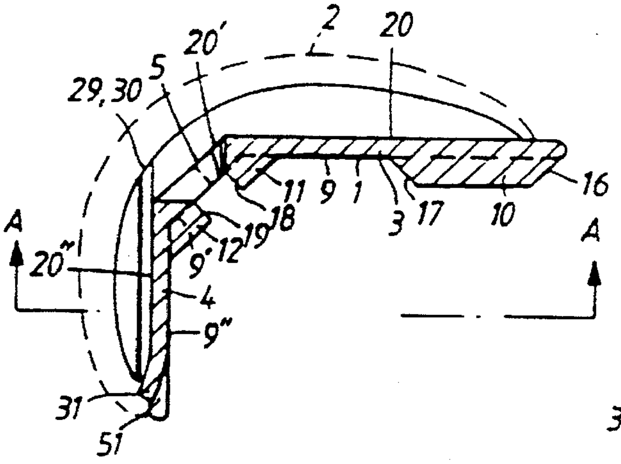
FIG. 3 shows a section along the line B—B in FIG. 1

In FIGS. 1–4, which illustrate the prosthesis with its two parts in different views, 1 designates the attachment part and 2 designates the articulation element. The attachment part 1 comprises two essentially planar parts, a first part 3 and a second part 4, which are oriented generally at an angle relative to each other. These two parts 3,4 are joined by means of a third intermediate planar part 5, which is somewhat thicker than the two other parts 3,4. The intermediate part 5 is, in its central part, provided with a countersunk through hole 6 intended for a screw 7 for attachment to a fixture 8 (cf. FIGS. 5–9).

The attachment part 1 has inner surfaces 9,9',9" intended to bear on the bone tissue. The inner surfaces 9,9',9" are provided with three guiding and stabilizing flanges 10–12 intended to fit into corresponding grooves 13–15 cut in the bone tissue (cf. FIG. 6). The first flange 10 is arranged in the frontal end of the first part 3 and is generally arranged parallel to the long sides of the first part. The flange 10 has two short sides 16,17 oriented at an angle relative to each other. A second flange 11 is arranged at the back of the first part 3 and at the intermediate part 5, having a short end 18 being flush with the edge of the hole 6. A third flange 12 is arranged in the frontal end of the second part 4 and at the intermediate part 5, and it has a short end 19 also being flush with the edge of the hole 6 opposite to the end 18 mentioned above.

The attachment part has also outer surfaces 20, 20', 20" intended to support the articulation element 2. The outer surfaces 20, 20', 20" are provided with two identical flanges 21,22 arranged on a respective side of the attachment part 1 which are oriented mainly in parallel with the direction of the articulational movement of the joint when the attachment part 1 has been fitted. The flanges 21,22 eqch have an outer surface 23,24 with a smooth rounded contour and an inner surface 25,26 oriented mainly perpendicularly to the outer surfaces 20, 20', 20" of the attachment part 1. Both flanges 21,22 are provided with a straight, elongate groove 27,28 extending along the outer surface 20" of the second part 4 over the entire extent of the respective flange 21,22. Each groove thus has one end 29,30 above the intermediate part 5 and and the other end at the end of the flanges 21,22.

In order to allow the articulation element 2 to be locked to the attachment part 1, the attachment part 1 is provided with a snap-action lock 31 located at the end of the back part 4. The snap-action lock 31 is in the shape of a resilient tongue, which is joined with the remainder of the second part 4 at one end and thus can thus lock the articulation element 2 by resiliently engaging a recess 51 on the inner surfaces 32,32',32" of the articulation element 2.

Figure 4:
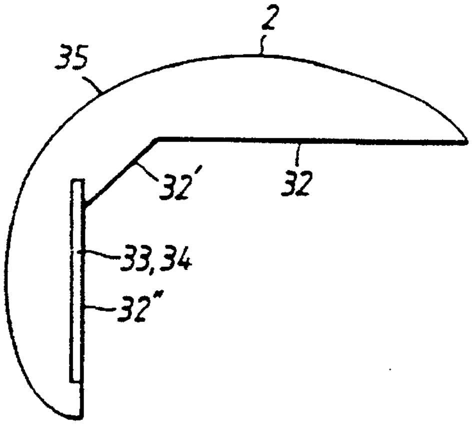
FIG. 4 shows the articulation element seen from one side.

The articulation element 2 can most easily be seen in FIG. 4, in which the element is illustrated in a side view. The element 2 has inner surfaces 32,32',32" intended to bear on the attachment part 1, said surfaces having a shape complementary to the outer surfaces 20, 20', 20" of the attachment part 1. The articulation element 2 is provided with two beads 33,34, each projecting from one respective side of the articulation element 2. They are intended to fit into the grooves 27,28 and have a shape complementary to the shape of the grooves 27,28. The outer surface 35 of the articulation element 2 is adapted to fit a meniscus to be used in combination with the prosthesis.

In FIG. 5–7 and 9 are the different parts of the joint illustrated during different phases of the operation. The first step is to accurately prepare the bone end for the implant by cutting the femoral bone tissue to have planar surfaces 36, 36',36" having a shape corresponding to the shape of the inner surfaces 9, 9', 9" of the attachment part 1. Then a hole 37 is drilled in the central surface of the recess 36'. A fixture 8, in the shape of a screw having an inner bore part 39 provided with internal threads is screwed into the hole 37. The fixture 8 is provided with transverse grooves 40–43 at its outer end. The fixture 8 is inserted in such a way that two of the grooves, in this case the grooves 40,41, are oriented mainly in parallel with the direction of the articulational movement of the joint, i.e. along the longitudinal direction of the attachment part 1. The next step is to cut the grooves 13–15. The two grooves 14,15 are cut as extensions of the two transverse grooves 40,41 in the fixture 8. The groove 13 is cut in the frontal end of the surface 36 in the bone tissue. The attachment part 1 is then placed on the surfaces 36, 36', 36", being guided to the correct position by the stabilizing flanges 10–12, which fit into the corresponding grooves 13–15, the flanges 11,12 at the same time fitting into the transverse grooves 40,41. In this way, the fixture is locked against rotation.

The attachment part 1 then is attached to the cut bone surface by means of an attachment screw 7 which is screwed into the fixture 8.

The final step is to connect the articulation element 2 to the attachment part 1. This is performed by fitting the beads 33,34 into corresponding elongate grooves 27,28 and sliding the articulation element 2 along the grooves 27,28 until the element abuts the outer surfaces 20,20',20' of the attachment part 1. When the articulation element 2 entirely has been slid on to the attachment part 1, it is locked by the snap-action lock 31. The operation is then completed.

In FIGS. 6—7 a second embodiment of the attachment part 1 is shown where a locking device corresponding to the snap-action lock 31 is arranged on each side of the flanges 21,22. This locking device is formed by those parts of the flanges 21,22 which are located between the perpendicular transverse slits 45–48 cut in each of the flanges 21,22. Grooves 49,50, extending in parallel to the outer surface 20 of the attachment part 1, are provided on the inner surfaces of the parts of the flanges 21,22 located between the transverse slits 45–48. By these means a kind of snap-action lock is formed functioning as a resilient tongue which can engage the articulation element 2 resiliently. When this embodiment is used, the articulation element will be provided with additional beads fitting into the horisontal grooves 49,50.

FIG. 8 shows a further embodiment of the invention wherein the outer surface 20, on that planar part 3 which is not parallel with the grooves 27,28, is provided with a conical plug 52 adapted to to fit into a complementary conical recess or cavity 53 provided in the inner surface 32 of the articulation element 2. This conical plug 52 will, in conjunction with the conical recess 53, further stabilize the articulation element 2 relative to the attachment part 1. This feature may be of particular interest when the flanges 21,22 are to function as resilient locking tongues.

The invention can of course be varied in many ways within the scope of the claims.

We claim:

1. A joint prosthesis requiring only one operation to be permanently anchored in the bone tissue of one of the articulating parts of a joint in a human body, in particular the femur side of a knee joint, said prosthesis comprising:

a) an attachment having an inner surface for bearing against the bone tissue and an outer surface, the attachment including:

a first and a second essentially planar part oriented generally at an angle relative to each other;

an intermediate part joining the planar parts; and flanges disposed on the outer surface over the planar parts and the intermediate part and oriented parallel to the direction of articulation movement of the joint, the flanges each having a groove disposed over and oriented parallel to the second planar part;

b) means for securing the attachment to the bone tissue;

c) an articulation element disposed over the outer surface of the attachment and having an interior shape which is complementary to the outer surface, the articulation element including beads projecting from opposed side surfaces of the articulation element and engaging the grooves; and d) locking means for fixing the articulation element to the attachment when the articulation element is disposed over the attachment and the beads are engaged in the grooves.

2. A joint prosthesis according to claim 1, further comprising a plurality of stabilizing flanges disposed on the inner surface of the attachment for fitting into complementary grooved areas cut in the bone tissue for guiding and stabilizing the attachment in the bone tissue.

3. A joint prosthesis according to claim 2, wherein the intermediate part has a countersunk through-hole located above a hole cut in the bone and the means for securing the attachment to the bone tissue comprises:

an externally threaded fixture for screwing into the hole cut in the bone tissue, the fixture including an inner bore provided with internal threads and an outer end disposed at the surface of the bone tissue when the fixture is screwed into the hole, the outer end having at least one transverse groove in line with one of the grooved areas cut in the bone tissue; and an attachment screw for being screwed into the inner bore of the fixture and having a head which sits in the countersunk through-hole for securing the attachment to the bone tissue;

wherein one of the stabilizing flanges on the inner surface of the attachment is fitted into at least one transverse groove to prevent the fixture from rotating.

4. A joint prosthesis according to claim 1, wherein the locking means is in the shape of a snap-action lock arranged in the second planar part being parallel with said grooves and comprises a resilient tongue extending from the second planar part and engaged to a recess on the interior of the articulation element.

5. A joint prosthesis according to claim 1, further comprising a conical plug disposed on the outer surface of the attachment for fitting into a complementary conical recess located on the interior surface of said articulation element.

* * * * *